United States Patent
Cragg et al.

(10) Patent No.: US 6,533,751 B2
(45) Date of Patent: Mar. 18, 2003

(54) MICRO CATHETER AND GUIDEWIRE SYSTEM HAVING IMPROVED PUSHABILITY AND CONTROL

(76) Inventors: Andrew Cragg, 4502 Edina Blvd., Edina, MN (US) 55424; James H. Kim, 17 Dominguez, Aliso Viejo, CA (US) 92656

(*) Notice: Subject to any disclaimer, the term of this patent is extended or adjusted under 35 U.S.C. 154(b) by 12 days.

(21) Appl. No.: 09/758,331

(22) Filed: Jan. 9, 2001

(65) Prior Publication Data

US 2002/0091372 A1 Jul. 11, 2002

(51) Int. Cl.[7] .............. A61M 31/00; A61M 29/00; A61M 25/00; A61M 5/00
(52) U.S. Cl. .............. 604/93.01; 604/264; 604/524; 604/525; 604/506; 604/507; 604/508; 604/96.01; 604/528; 604/533; 604/537
(58) Field of Search ............... 604/264, 524, 604/525, 528, 533, 537, 93.01, 96.01, 506–508; 600/194, 434, 435, 585

(56) References Cited

U.S. PATENT DOCUMENTS

| | | | |
|---|---|---|---|
| 4,739,768 A | | 4/1988 | Engelson |
| 5,304,198 A | | 4/1994 | Samson |
| 5,318,529 A | | 6/1994 | Kontos |
| 5,348,537 A | | 9/1994 | Wiesner et al. |
| 5,425,723 A | * | 6/1995 | Wang .......................... 604/280 |
| 5,823,198 A | * | 10/1998 | Jones et al. ................. 128/899 |
| 5,873,865 A | * | 2/1999 | Horzewski et al. ......... 604/280 |
| 5,888,436 A | * | 3/1999 | Keith et al. ................. 264/103 |
| 5,951,494 A | * | 9/1999 | Wang et al. ................. 600/585 |
| 6,179,809 B1 | * | 1/2001 | Khairkhahan et al. ... 604/95.04 |
| 6,312,374 B1 | * | 11/2001 | von Hoffmann ................ 600/3 |

* cited by examiner

Primary Examiner—Timothy L. Maust
Assistant Examiner—Anuradha Ramana
(74) Attorney, Agent, or Firm—Burns, Doane, Swecker & Mathis, L.L.P.

(57) ABSTRACT

A micro catheter and guidewire system for use in tortuous regions of a vasculature includes a catheter body having a distal end, a guidewire lumen, a proximal region with an outer diameter, and a distal region with an outer diameter. The ratio of the proximal region outer diameter to the distal region outer diameter is at least 1.625:1 to improve pushability of the catheter body. The guidewire lumen defines a stopper and the guidewire has a depth stop for engaging the stopper of the guidewire lumen. The depth stop and the stopper cooperate to enable the guidewire to cooperate with the catheter to improve catheter pushability. The depth stop and the stopper also prevent over extension of the guidewire.

6 Claims, 4 Drawing Sheets

MICRO CATHETER AND GUIDEWIRE SYSTEM HAVING IMPROVED PUSHABILITY AND CONTROL

FIELD OF THE INVENTION

This invention relates intravascular catheters, and more particularly to micro catheters and guidewires that access tortuous regions of the vasculature.

BACKGROUND OF THE INVENTION

There is a demand for increasingly smaller diameter catheters to enable access to tortuous regions of the vascular system such as regions of the neurovasculature.

Tortuous regions of the vasculature are defined as regions having vessels that branch off from more proximal vessels at angles of greater than 90 degrees. Portions of the vessels have lumen diameters of 3 mm or less. Micro catheters are defined as those catheters capable of navigating through these tortuous regions. There are limitations to the functionality of existing micro catheters.

One limitation relates to pushability of micro catheters. Typically micro catheters are inserted into the vasculature with a guiding catheter. As micro catheters evolve into smaller sizes, it is found that a micro catheter can kink or buckle when tracking via the guiding catheter. Kinking and buckling of a micro catheter are not desirable qualities.

Many micro catheters have a braided catheter body to reinforce the catheter body, optimizing catheter pushability and thereby inhibiting buckling. Current braided catheter technology has proved useful with the larger micro catheters; e.g. micro catheters having a 0.032" distal shaft diameter and larger.

Braided catheters, particularly for micro catheters having distal shaft diameters of less than 0.032", are expensive to manufacture and may be cost prohibitive to use regularly. Braided catheters may not bend well enough for use in the most distal and tortuous regions of the vasculature. What is desired is a micro catheter that has a high degree of axial compressive strength (pushability) and the capability to bend through tortuous regions of the vasculature. What is also desired is a micro catheter that resists kinking and buckling.

SUMMARY OF THE INVENTION

A micro catheter and guidewire system for use in tortuous regions of a vasculature includes a catheter body having a distal end, a guidewire lumen, a proximal region with an outer diameter, and a distal region with an outer diameter.

The ratio of the proximal region outer diameter to the distal region outer diameter is at least 1.625:1 to strengthen the proximal region, thereby improving the overall integrity of the catheter body. Increased torque capability, improved pushability and increased control of the catheter body result from forming the catheter body according to this ratio. Strengthening the proximal region further enables the catheter body to resist kinking and buckling during use.

The guidewire lumen defines a stopper and the guidewire has a depth stop for engaging the stopper of the guidewire lumen. The stopper in the guidewire lumen and depth stop on the guidewire enable the guidewire to selectively and compositely cooperate with the catheter to improve catheter pushability when the depth stop and the stopper engage.

The depth stop and stopper cooperate to prevent over extension of the guidewire when the guidewire and catheter body simultaneously push through tortuous regions of the vasculature.

The guidewire lumen defines a pathway between the guidewire and the guidewire lumen to facilitate infusion of fluids including contrast agents, blood thinners, nutrients, and medicine through the distal end of the catheter body. This is important because a separate infusion lumen, which consumes space, is not necessarily required. The depth stop and stopper function as a valve to prevent the infusion of fluid via the pathway.

BRIEF DESCRIPTION OF THE DRAWING

The present invention is described by way of example in the following figures where like parts have like reference numerals and wherein:

FIG. 2a shows the catheter of FIG. 1 inserted into a patient.

FIG. 2b shows an expanded view of a portion of FIG. 2a

DETAILED DESCRIPTION

Figure 1:
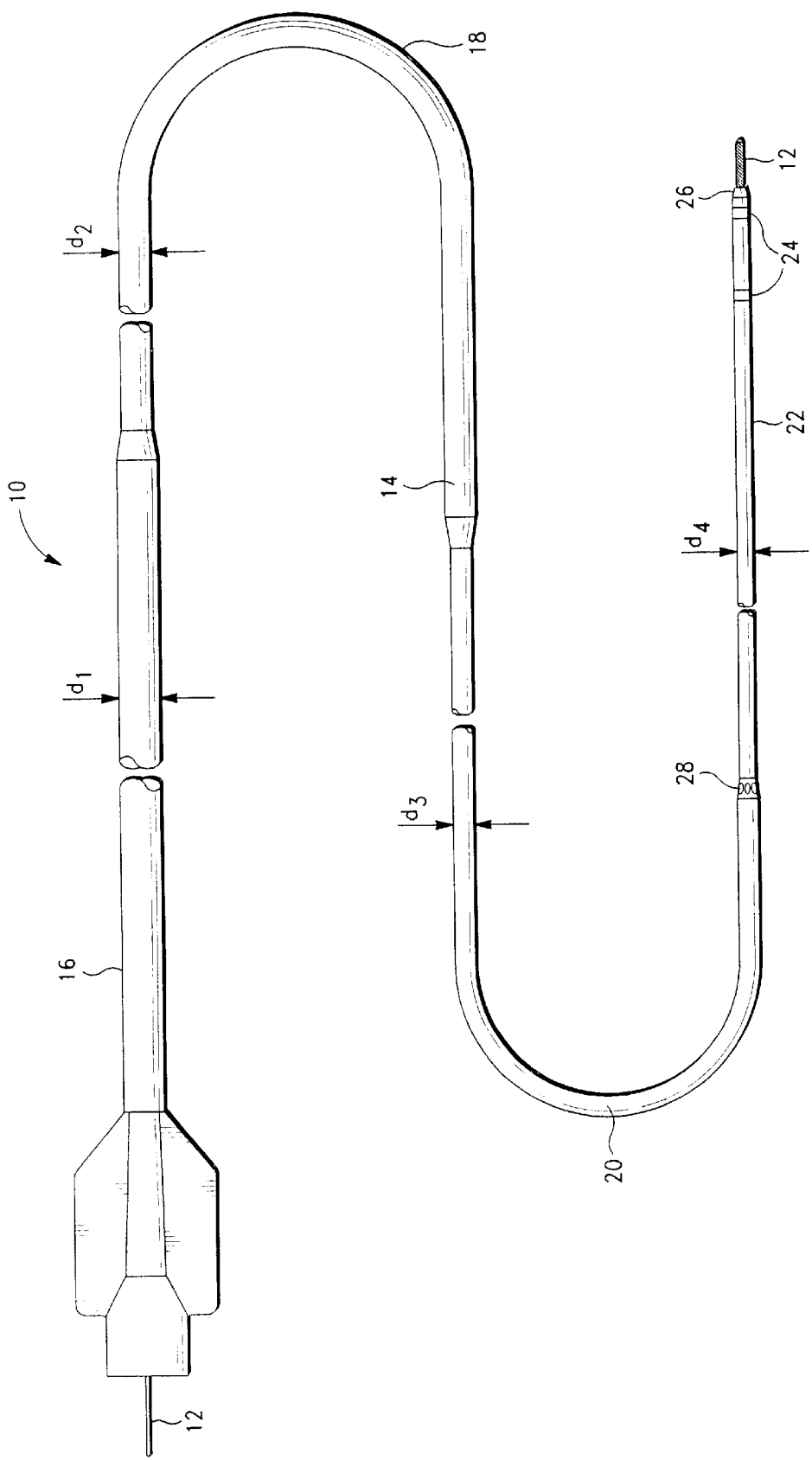
FIG. 1 shows a catheter and guidewire in accordance with the present invention.

FIG. 1 shows an intravascular catheter, generally designated with the reference numeral 10. The catheter 10 includes a guidewire 12 extending through the catheter 10. The catheter 10 includes a hollow catheter body 14 having a proximal region 16, a first intermediate region 18, a second intermediate region 20, and a distal region 22.

The distal region 22 includes marker bands 24 to facilitate identification of the distal region 22 when the catheter inserts into the vasculature of a patient. The catheter body has a distal end 26 defined on the distal region 24. The guidewire 12 extends from the distal end 26 when the guidewire 12 inserts through the catheter 10.

The catheter 10 can be designed to have any of a number of therapeutic or diagnostic functions. Preferably, the catheter body 14 includes an infusion lumen with ports 28 that facilitate direct delivery of fluids to the blood stream of a patient. Such fluids include nutrients, blood thinners, medicine, contrast agent, or other fluid useful in diagnosis and treatment of the patient.

The catheter body 14 is tubular, having a circular cross section. Each region 16, 18, 20, and 22 forms a discrete segment, having an outer diameter $d_1$, $d_2$, $d_3$, and $d_4$, respectively. The proximal region is bolstered in size and integrity with respect to the distal region. The ratio of the proximal region outer diameter $d_1$ to the distal region outer diameter $d_4$ is at least 1.625:1.

Bolstering the proximal region 16 improves not only the local strength of the proximal region 16, but importantly, improves the overall strength of the catheter body 14. Improving the overall strength of the catheter body 14 by bolstering the proximal region 16 results in measurable improvements in catheter 10 pushability, backup ability, torque transfer capability and control. Bolstering the proximal region 16 makes the distal region 22 resist kinking or buckling while accessing tortuous regions of the vasculature.

It can be appreciated that while bolstering the proximal region 16 is accomplished, according to the present invention, by increasing the proximal region diameter $d_1$, there are other ways of bolstering the proximal region 16. Such ways include providing a proximal region of a relatively stronger material (as compared with the material of the distal region), or otherwise reinforcing the proximal region 16. Increasing the proximal region diameter $d_1$ is preferred to these other techniques because it is simpler to accomplish, and it works.

An optimal catheter design, according to the present invention, has the ratio of the proximal region 16 outer diameter $d_1$ to the distal region 22 outer diameter $d_4$ of at least 1.625:1. This geometry proves useful alone, or in combination with using materials of varying strengths and flexibility for each of the regions 16, 18, 20 and 22. Braided reinforcement is used to further strengthen selected segments of the catheter body 14, as necessary.

Preferably, the catheter body 14 is constructed of thermoplastic materials where the proximal region 16 has the most rigid composition, and the distal region 22 has the softest composition. The composition of the intermediate regions 18 and 20 results in decreasing catheter body 14 stiffness between the proximal region and the distal region.

It can be appreciated that while two intermediate regions 18 and 20 are shown it is possible, and perhaps desirable, to have more, or less, intermediate regions. Further, while the intermediate regions 18 and 20 form discrete segments, the catheter body 14 can also taper from the proximal region 16 to the distal region 22 without the need for discrete segments. Design considerations such as catheter length, and particular application can dictate the appropriate number of intermediate regions, geometry, flexibility and composition of such regions.

A prototype of the invention tested to have regions of relative stiffness as follows: the proximal region 16 has a stiffness of 0.004–0.0020 in/lb at 30 degree deflection at span of 0.05" with a 0.025 lb weight; the first intermediate region 18 has a stiffness of 0.0020–0.0080 in/lb at 30 degree deflection at span of 0.105" with a 0.025 lb weight deflection; the second intermediate region 20 has a stiffness of 0.0020–0.0040 in/lb at 30 degree deflection at span of 0.05" with a 0.080 lb weight; and the distal region 22 has a stiffness of 0.0030–0.0070 in/lb at 30 degree deflection at span of 0.05" with a 0.080 lb weight. It can be appreciated that while these figures are reflective of stiffness values for a particular micro catheter 10 in accordance with the present invention (i.e. a micro catheter 10 having a distal region outer diameter of 0.032" or less) these stiffness figures for micro catheter designs of very small sizes may be softer than these exemplarily stiffness ranges.

While the stiffness of each region of the catheter body 14 can be measured under lab conditions, there are other ways of representing the relative stiffness of the various regions of the catheter body 14, such as in terms of material composition and geometry.

One preferable geometry of the catheter body 14 has a usable length of between 120–180 cm. The proximal region 16 has a 3.0F–5.0F outer diameter $d_1$, and an 80–130 cm length. More preferably, the proximal region 16 has a 4.0F–5.0F (0.052"–0.065") outer diameter $d_1$. The first intermediate region 18 has a 2.5F–5F outer diameter $d_2$ and a 2–10 cm length. The second intermediate 20 region has a 2.0F–4.5F outer diameter $d_3$ and a 5–20 cm length.

The distal region 22 has a 1.2F–2.5F outer diameter $d_4$ and a 5–20 cm length. It can be appreciated that the distal end 26 of the catheter body 14 can be contoured, stepped or otherwise deviate from the average dimension $d_4$. Accordingly, the $d_4$ value generally referred to herein is the nominal dimension of the whole 5–20 cm length of the distal region 22 without regard to contours, steps or other deviations that may be present on the distal region 22, particularly near the distal end 26.

The distal region outer diameter $d_4$ is a maximum of 2.5F (0.032") to enable use of the catheter body in tortuous regions of the vasculature and the proximal region has a minimum outer diameter $d_1$, of 4.0F (0.052") to optimize catheter body pushability.

According to one aspect of the invention, the catheter body 14 includes an infusion lumen and infusion ports 28. Preferably, the infusion ports 28 are located in a transition region defined between the second intermediate region 20 and the distal region 22. While FIG. 1 shows infusion ports 28 at a single location, it can be appreciated that any transition region between discrete catheter segments may include infusion ports 28 in accordance with the present invention.

Figure 2:
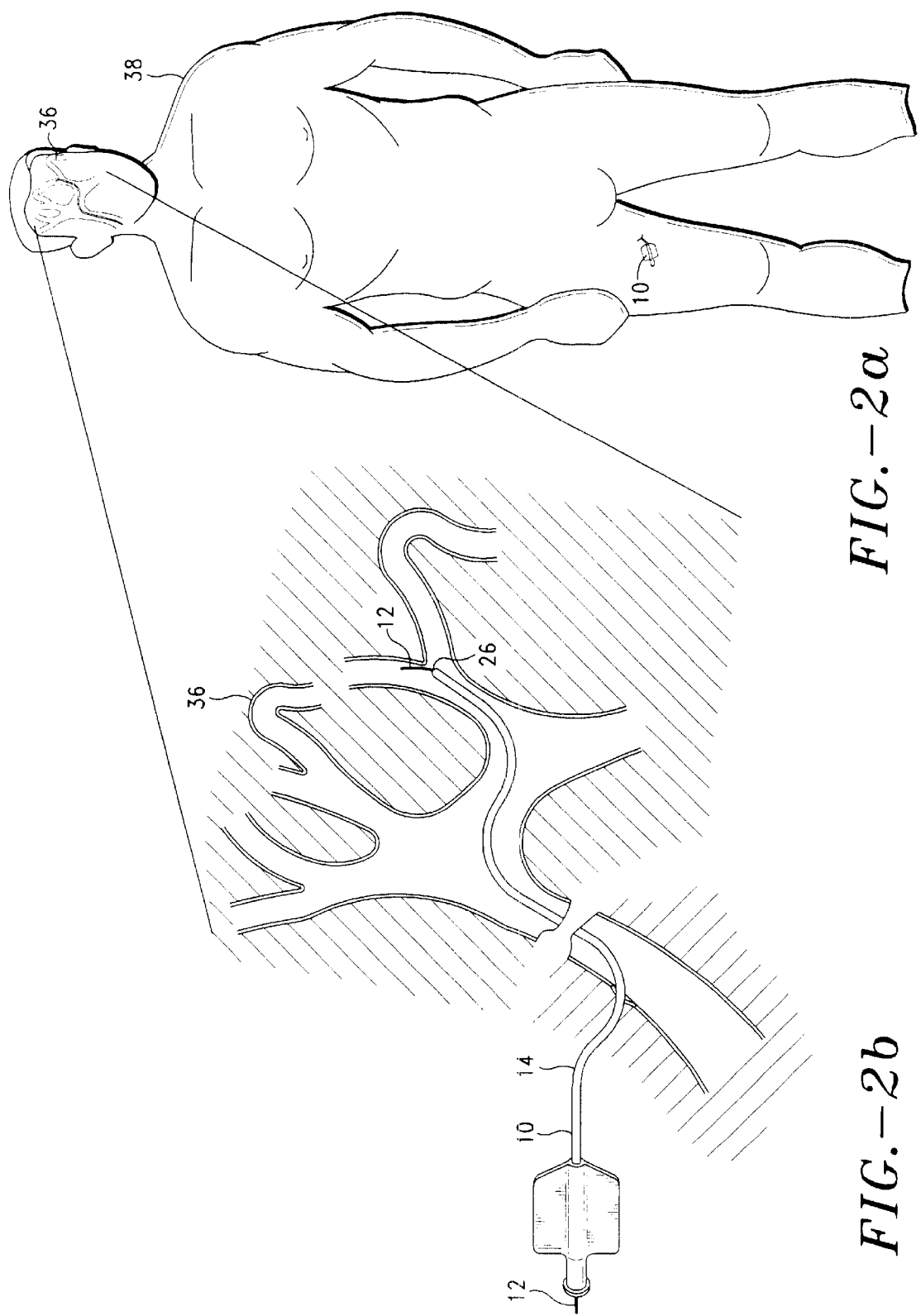

FIG. 2a and FIG. 2b show the micro catheter 10 inserted into the vasculature 36 of a patient 38. A method of using the catheter 10 in tortuous regions of the vasculature 36 includes providing the catheter body 14, disposing a guidewire 12 into the catheter body 14 and extending the guidewire 12 beyond the distal end 26 of the catheter 10. The method includes the steps of simultaneously advancing the guidewire 12 and catheter body 14 into the vasculature 36 of the patient 38. The method step of limiting the extension of the guidewire 12 with a depth stop prevents over extension of the guidewire 12.

Preventing over extension of the guidewire 12 prevents the guidewire 12 from unnecessarily disrupting the compliant tissues of the vasculature 36. Limiting the extension of the guidewire 12 enables the guidewire to help "push" the catheter body 14 through the vasculature 36.

The method includes step of infusing fluid through the catheter body 14, via the infusion port 28, into the vasculature. The step of advancing the catheter 10 includes advancing the catheter 10 into tortuous regions of the neurovascualture.

The method further includes the step of detecting the marker bands 24 (FIG. 1) to determine where the distal end 26 is located within the vasculature 35.

The catheter body 14 has a guidewire lumen (supra) defining a pathway that functions as an infusion lumen. The method further comprises the step of delivering contrast media, medicine, nutrition, or a blood thinning agent through the distal end 26 of the catheter body 14 via the pathway.

Figure 3:
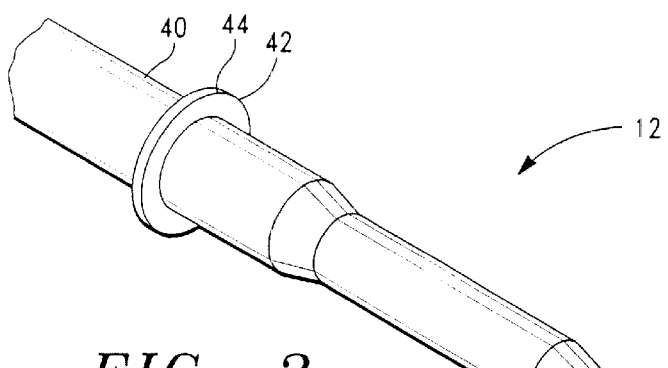
FIG. 3 shows an embodiment of a guidewire in accordance with the present invention.

FIG. 3 shows a distal end 40 of the guidewire 12. The distal end 40 has a depth stop 42 for preventing the guidewire from over-extending from the catheter. According to one aspect of the invention, the depth stop 42 defines an annular flange 44 that aligns coaxially with the distal end 40. It can be appreciated that though an annular flange 44 is shown for preventing over-extension of the guidewire, the depth stop 42 can take other shapes. For example, the depth stop 42 can take the shape of a generally spherical bulb, a series of ridges, a frustum aligned coaxially on the distal end, or any other shape that would prevent over-extension.

Figure 4:
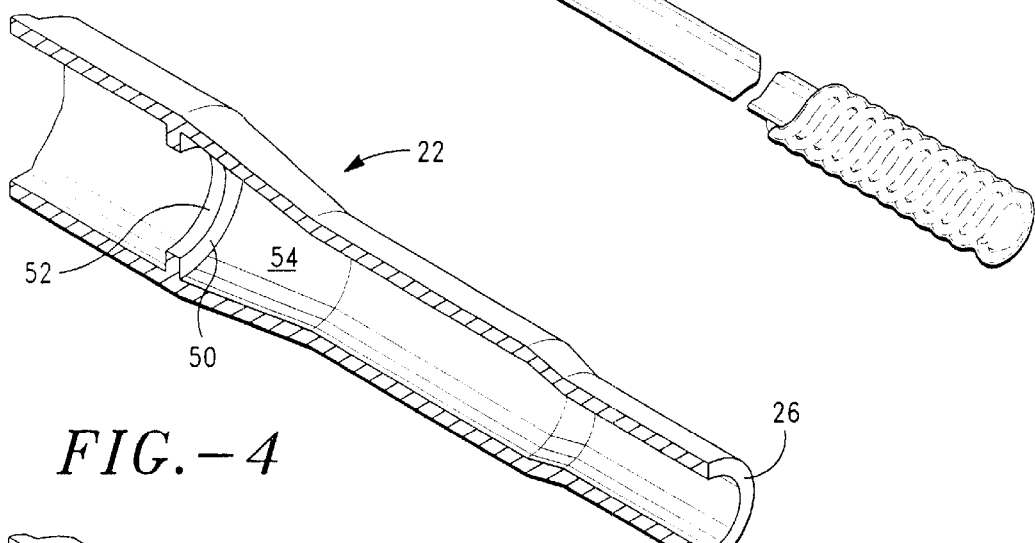
FIG. 4 shows the distal end of a catheter body in accordance with the present invention.

FIG. 4 shows the distal region 22 of the catheter body 14. The distal region 22 includes a stopper 50 that selectively engages the depth stop 42 of the guidewire 12. The stopper 50 defines annular flange 52 that meets the guidewire depth stop 42 annular flange 44 to prevent over extension of the guidewire 12 through the distal end 26 of the catheter body 14 (FIG. 1).

The catheter body 14 defines a guidewire lumen 54 within the catheter body 14. The stopper 50 is fixed within the guidewire lumen 54 and has an opening to permit a guidewire to pass through the stopper 50.

With reference to FIG. 1, FIG. 2a, FIG. 2b, FIG. 3 and FIG. 4, it can be appreciated that pressing the guidewire depth stop 42 against the stopper 50 of the catheter body 14 improves the catheter body 14 pushability and inhibits buckling and kinking of the distal region 22 of the catheter body 14. This is possible because when the guidewire 12 (FIG. 1) fully extends from the catheter body 14, and the depth stop 42 presses against the stopper 50, the guidewire 12 and the catheter body 14 act in composite cooperation. Simultaneous insertion of the guidewire 12 and the catheter body 14 into the tortuous regions of the neuro-vasculature is enabled because the guidewire 12 reinforces the catheter body 14, particularly the distal region 22 of the catheter body 14.

Pressing an annular depth stop 42 against and an annular stopper 50 inhibits deformation, (e.g. expansion) of the outer diameter $d_4$ of the distal region 22. However, it can be appreciated that various other depth stop 42 and stopper 50 designs would inhibit such deformation. It should also be noted that a limited degree of deformation is not always objectionable.

Figure 5:
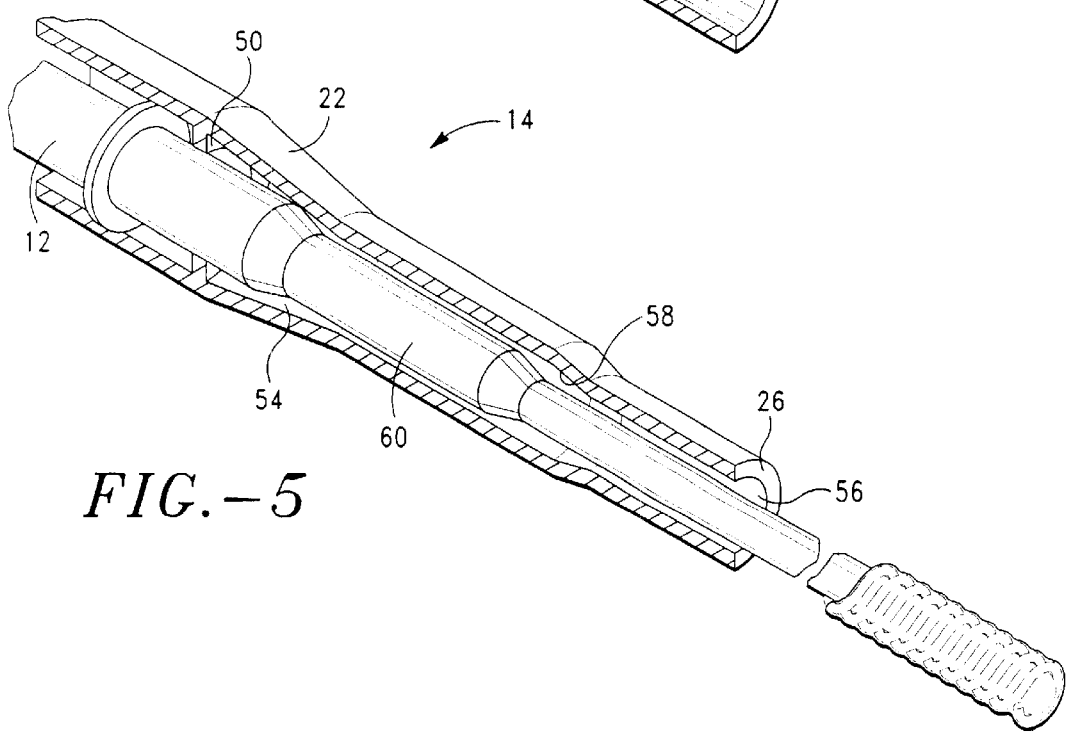
FIG. 5 shows the guidewire of FIG. 3 within the catheter body of FIG. 4.

FIG. 5 shows the distal region 22 of the catheter body 14. The guidewire 12 extends through the guidewire lumen 54. The catheter body 14 forms a pathway 56 within the guidewire lumen 54, between the guidewire 12 and the guidewire lumen 54. The pathway 56 facilitates infusion of fluid through the distal end 26, which functions as an infusion port.

The guidewire lumen 54 has a stepped interior 58. The guidewire 12 has a stepped exterior 60 that corresponds with the stepped interior 58 of the guidewire lumen 54. The stepped exterior 60 is offset from the stepped interior 58 when the depth stop 42 of the guidewire 12 meets the stopper 50 of the catheter body 14. Offsetting the stepped exterior of the guidewire with the stepped interior of the depth stop 42 prevents the guidewire 12 from radially deforming the distal region 22 and the distal end 56 of the catheter body 14.

Figure 6:
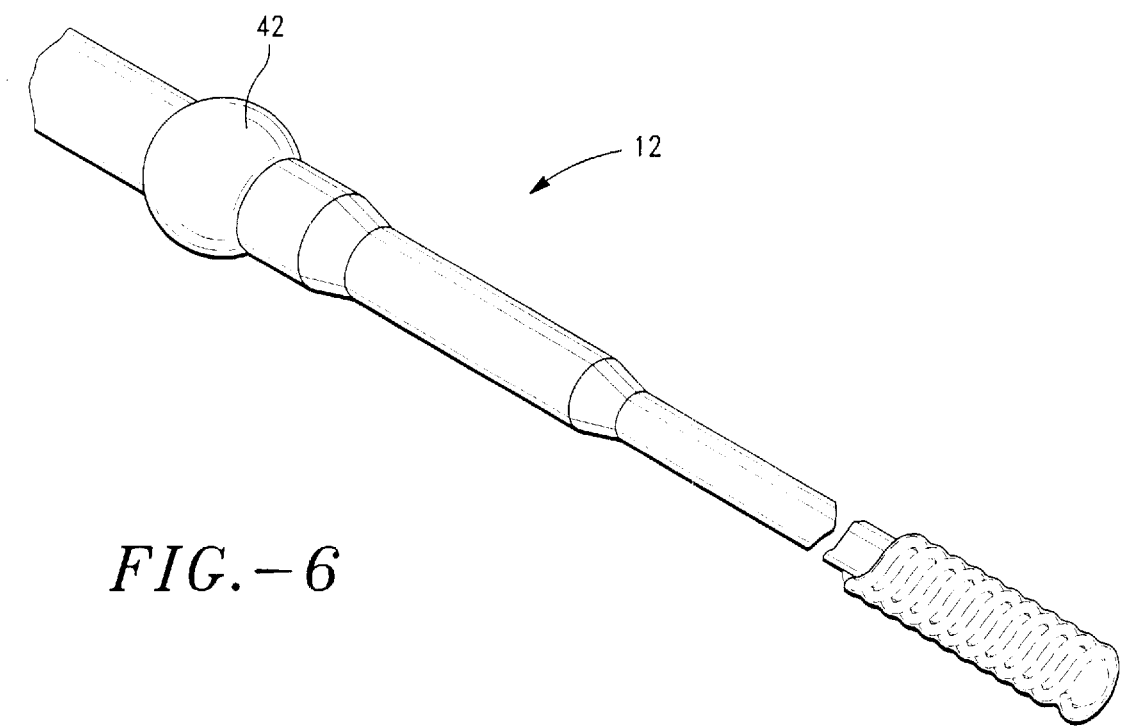
FIG. 6 shows an embodiment of a guidewire in accordance with the present invention.

FIG. 6 shows an embodiment of the guidewire 12. The depth stop 42 includes a bulb 42 formed on the guidewire 12.

The present invention is described in terms of a preferred embodiment, however, it can be appreciated that the present invention can be modified to achieve various goals. For example, the ability of the guidewire to act as a valve can enable selective pressurization of the catheter body by infusion fluids to facilitate selective changes in catheter flexibility. These pressure changes in conjunction with selective reinforcement of the catheter body by the guidewire, and bolstering of the proximal region by the geometry and ratio described herein can result in smaller micro catheters with improved pushability. Further modifications to the configuration and ratio between the proximal region and distal region can also improve pushability in small micro catheters. The configuration of the stopper and the depth stop can be modified, and improved so that the guidewire can add more to the pushability of the catheter. Accordingly, the present invention is to be limited only by the following claims:

What is claimed is:

1. A micro catheter for use in tortuous regions of a vasculature, comprising:
   a catheter body having a bolstered proximal region with an outer diameter, and a distal region having an outer diameter; and
   the proximal region outer diameter has a ratio to the distal region outer diameter of at least 1.625:1,
   whereby bolstering the proximal region strengthens the catheter body to improve pushability of the micro catheter, wherein the distal region outer diameter is a maximum of 0.032" and the proximal region outer diameter is a minimum of 0.052" to optimize pushability while enabling use in tortuous regions of the vasculature.

2. A micro catheter as set forth in claim 1, wherein the catheter body defines a guidewire lumen, a distal end, and a stopper formed within the guidewire lumen.

3. A micro catheter as set forth in claim 1, wherein the stopper includes an annular flange.

4. A micro catheter as set forth in claim 3, wherein the stopper is formed in the distal region of the catheter body.

5. A micro catheter as set forth in claim 4, wherein the catheter body has a distal end, the guidewire lumen defines a pathway for infusing fluids via the distal end.

6. A micro catheter as set forth in claim 5, wherein the catheter body includes a first intermediate region and a second intermediate region sequentially defined between the proximal region and the distal region, respectively, the catheter body includes infusion ports are located between the second intermediate region and the proximal region of the catheter body.

* * * * *